United States Patent [19]

Horodysky

[11] 4,450,096

[45] May 22, 1984

[54] METAL HYDROCARBYL PHOSPHORODITHIOATES AND LUBRICANTS CONTAINING SAME

[75] Inventor: Andrew G. Horodysky, Cherry Hill, N.J.

[73] Assignee: Mobil Oil Corporation, New York, N.Y.

[21] Appl. No.: 350,691

[22] Filed: Feb. 22, 1982

[51] Int. Cl.³ .............................................. C10M 1/48
[52] U.S. Cl. ........................... 252/32.7 E; 260/429.9; 260/937; 260/981; 260/950; 260/953
[58] Field of Search ................ 252/32.7 E; 260/429.9, 260/125, 937, 981, 950, 953

[56] References Cited

U.S. PATENT DOCUMENTS

| | | | |
|---|---|---|---|
| 3,089,850 | 5/1963 | McConnell et al. | 260/937 |
| 3,159,664 | 12/1964 | Bartlett et al. | 260/937 |
| 3,396,183 | 8/1968 | Brasch | 260/937 |

*Primary Examiner*—Jacqueline V. Howard
*Attorney, Agent, or Firm*—Alexander J. McKillop; Michael G. Gilman; Claude E. Setliff

[57] ABSTRACT

Multifunctional additives are provided for fuel and lubricant compositions. The additives are products prepared from metal-containing compounds, phosphorus polysulfides and hydrocarbyl vicinal diols. The lubricants include mineral oils, synthetic oils, mixtures thereof and greases from either of the three types.

17 Claims, No Drawings

METAL HYDROCARBYL PHOSPHORODITHIOATES AND LUBRICANTS CONTAINING SAME

BACKGROUND OF THE INVENTION

1. Field of the Invention

The invention relates to lubricant and liquid fuel compositions. In particular, it relates to metal hydrocarbyl vicinal diol phosphorodithioates and their use in lubricants to reduce friction and fuel consumption in internal combustion engines.

2. Discussion of the Prior Art

Alcohols are well known for their lubricity properties when formulated into lubricating oils and greases. The use of vicinal hydroxyl-containing alkyl carboxylates such as glycerol monooleate have also found widespread use as lubricity additives. U.S. Pat. No. 2,788,326 discloses some of the esters suitable for the present invention, e.g. glycerol monooleate, as minor components of lubricating oil compositions. U.S. Pat. No. 3,235,498 discloses, among others, the same ester as just mentioned, as an additive to other oils. U.S. Pat. No. 2,443,578 teaches esters wherein the free hydroxyl is found in the acid portion, as for example in tartaric acid.

U.S. Pat. No. 4,044,032 teaches metal salts of certain products made by reacting an alkoxylated alcohol, a polysulfide and a metal sulfide to make additives, but no art is known relating to the compounds of this invention.

SUMMARY OF THE INVENTION

In accordance with the present invention there is provided a lubricant composition comprising a major proportion of a lubricant and a friction reducing amount of the reaction product obtained by reacting a hydrocarbyl vicinal diol with a phosphorus polysulfide, such as phosphorus pentasulfide followed by reacting this product with a metal oxide or metal salt. The hydrocarbyl vicinal diol will contain 12 to 20 carbon atoms. In such compositions, the product can be used in friction reducing amounts, which can range from about 0.1% by weight to about 5.0% by weight in lubricants. "Hydrocarbyl" includes straight chain or branched chain alkyl, alkenyl, cycloalkyl, cycloalkenyl, preferably alkyl or alkenyl, and more preferably linear alkyl.

BACKGROUND OF THE INVENTION

The hydrocarbyl vicinal diols contemplated for use in this invention are hydrocarbyl diols having vicinal hydroxyls. They have the formula:

$$R(OH)_2$$

wherein R is a hydrocarbyl group as defined above. R can be linear or branched, saturated or unsaturated. The two hydroxyl groups are preferably near the end of the hydrocarbyl chain and are on adjacent carbon atoms (vicinal).

Among the diols contemplated are 1,2-hexadecanediol 1,2-tetradecanediol, 1,2-dodecanediol, 1,2-pentadecanediol, 1,2-heptadecanediol, 1,2-octadecanediol, mixed 1,2-$C_{15}$-$C_{18}$ alkanediols, and mixtures of all such diols including mixtures of similar diols.

The vicinal diols can be synthesized using several methods known to the art. One such method, described in an article in J. Am. Chem. Soc., 68, 1504 (1946), involves the hydroxylation of 1-olefins with peracids. Vicinal diols can also be prepared by the peroxytrifluoroacetic acid method for the hydroxylation of olefins as described in J. Am. Chem. Soc., 76, 3472 (1954). Similar procedures can be found in U.S. Pat. No. 2,411,762, U.S. Pat. No. 2,457,329 and U.S. Pat. No. 2,455,892. These are incorporated herein by reference.

The diols can also be prepared via catalytic epoxidation of an appropriate olefin, followed by hydrolysis.

As disclosed hereinabove, the preferred vicinal diols contain 12 to 20 carbon atoms. This range is preferred because diols having less than 12 carbon atoms have significantly less friction reducing properties, while in those having more than 20 carbon atoms solubility constraints become significant. Preferred are the $C_{14}$-$C_{18}$ hydrocarbyl groups in which solubility, frictional characteristics and other properties are maximized.

As disclosed hereinabove, the diols are used in lubricating oils in friction reducing amounts. Stated another way they can be used to the extent of from about 0.1% to about 5% by weight of the total composition, preferably about 1 to about 2% by weight. Furthermore, other additives, such as detergents (dispersants), antioxidants, anti-wear agents extreme pressure additives, pour depressants, antirust additives and the like may be present. These include phenates, sulfonates, succinimides, zinc dithiophosphates, polymers and the like.

The phosphorus polysulfide preferred in making the reaction product of this invention is phosphorus pentasulfide.

Metal cations used to prepare the salts of this invention may be derived from several conventional sources, for example from metal acid (both organic and inorganic) salts and metal oxides, hydroxides, carbonates, chlorides and the like. Such metals may be from Groups IB, IIB, VIA and VIII of the Periodic Table. These can include from the respective groups, silver, cadium, and zinc, molybdenium and nickel. Mixtures of these may also be used.

The following illustrates what are believed to be the major reactions taking place. The structures shown are believed to represent the major possible products. Since the product is a mixture of compounds, the claims will refer to them as reaction products. In the reactions illustrated a linear alkyl terminal vicinal diol (derived from the appropriate 1-olefin via epoxidation and subsequent hydrolysis) is phosphosulfurized by reaction with phosphorus pentasulfide ($P_2S_5$), in one of the solvents mentioned hereinbelow, if desired. The intermediate phosphorodithioic acids (I to IV) are metallized by treatment with one or more metal salts, such as zinc oxide, in the presence of a suitable solvent to give a mixture of products believed to comprise compounds V-IX. The useful solvents include hydrocarbon solvents such as toluene, benzene, xylene, heptane and other relatively unreactive solvents, including 1,4-dixoane and alcoholic solvents such as propanol or butanol. Mixtures of hydrocarbon solvents and other solvents are also useful.

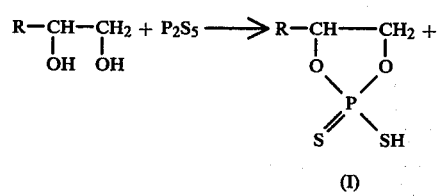

(I)

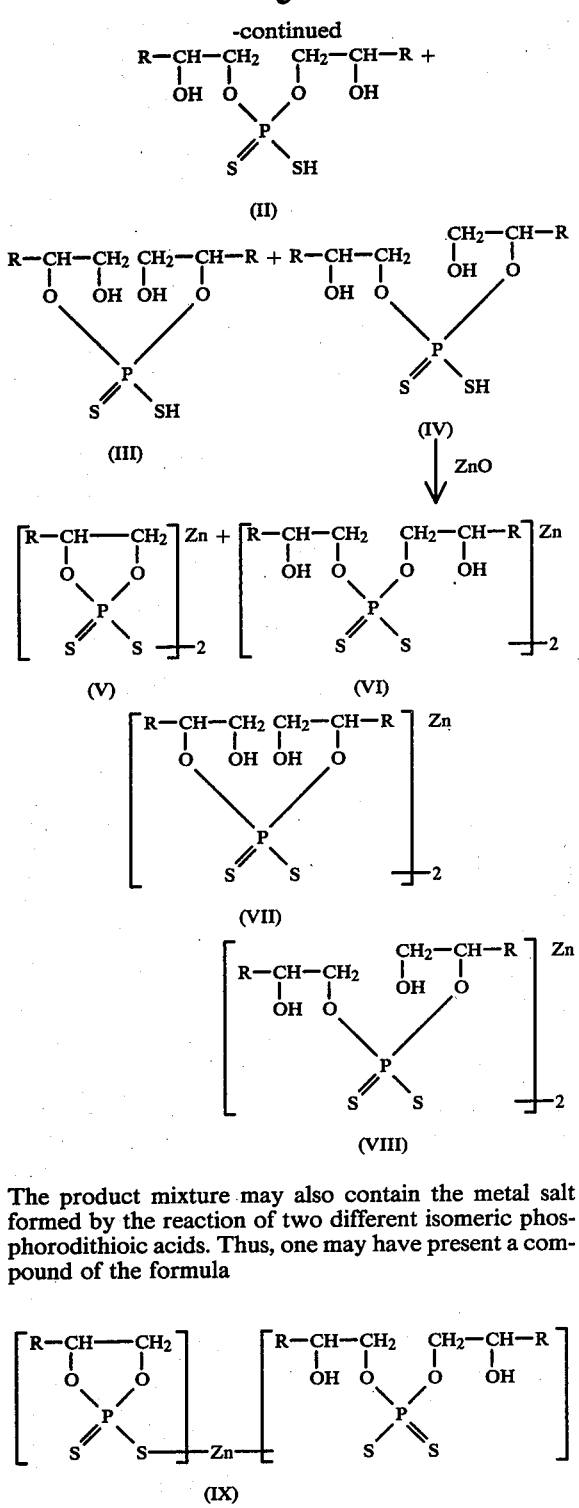

The product mixture may also contain the metal salt formed by the reaction of two different isomeric phosphorodithioic acids. Thus, one may have present a compound of the formula These illustrations show the reaction of 2 molecules of phosphorodithioic acid with a divalent zinc cation. The first reaction, i.e., between the diol and phosphorus polysulfide can be carried out at from about 40° C. to about 140° C., preferably from about 60° and about 90° C. The temperature chosen will depend for the most part on the particular reactants and on whether or not a solvent is used. In carrying out this reaction, it is preferable that quantities of reactants be chosen such that the ratio of diol to phosphorus polysulfide be from about 6 to 1 to about 1½ to 1. For example, in the reaction illustrated, from 2 to 4 moles of diol to one mole of $P_2S_5$ are employed. If the ratio is less than 2 to 1, the polysulfide will remain and can be filtered away. If the ratio is more than 4 to 1, excess diol will remain and will be carried through the reaction. Removal of unreacted diol may not be necessary, and in some cases may even be beneficial to form a partially phosphosulfurized hydrocarbyl diol.

The final reaction, i.e., with the metal-containing compounds, can be carried out at from about 40° C. to about 170° C., preferably from about 60° C. to about 95° C. The ratio of acid to metal compound may range from a stoichiometric amount, depending upon the valence of the cation, to as much as a 50% or more excess of metal compound. Any excess metal cation can be removed after the metallization step is completed.

While atmospheric pressure is generally preferred, the reactions can be advantageously run at from about 1 to about 3 atmospheres. Furthermore, both reactions can be advantageously affected by adding a small amount of water to the solvent used.

The times for the reactions are not critical. Thus, any phase of the process can be carried out in from about 1 to about 20 hours.

Besides reducing friction, these compositions exhibit antioxidant activity, good control of copper strip corrosivity and potential antiwear performance.

The lubricants contemplated for use with the esters herein disclosed include mineral and synthetic hydrocarbon oils of lubricating viscosity, mixtures of mineral and synthetic oils and greases from any of these. The synthetic hydrocarbon oils include long chain alkanes such as cetanes and olefin polymers such as oligomers of hexane, octene, decene, and dodecene, and the like. The other synthetic oils, which can be used alone with the compounds of this invention, or which can be mixed with a mineral and synthetic hydrocarbon oil, or mixtures thereof, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

Having described the invention in general terms, the following are offered to specifically illustrate the development. It is to be understood they are illustrations only and that the invention shall not be limited except by the appended claims.

EXAMPLE 1

Phosphosulfurized 1,2-Hexadecanediol

Commercially obtained 1,2-hexadecanediol and phosphorus pentasulfide were used. Approximately 250 g of 1,2-hexadecanediol and 500 g of toluene solvent were added to a 3 liter glass reactor fitted with agitator and caustic scrubber in the off-gas line. The reaction mixture was heated to about 70° C. with agitation and 56 g of phosphorus pentasulfide was added over a period of one hour. Hydrogen sulfide evolution was noted. The reaction mixture was then heated to 85° C. and held there for 4 additional hours with agitation and with a slow nitrogen purge over the vapor space. The mixture was filtered to remove any unreacted phosphorus pentasulfide.

EXAMPLE 2

Zinc Salt of Phosphosulfurized 1,2-Hexadecanediol

Approximately 260 g of the solvent-diluted phosphosulfurized 1,2-hexadecanediol described in Example 1 was charged to a 500 ml glass reactor and warmed to about 65° C. Approximately 25 g of 2-propanol and 7.5 g of zinc oxide were added. The reaction mixture was stirred @ 90° C. for 6 hours. The solvents were removed by vacuum distillation @ 90° C. and the zinc salt was filtered through diatomaceous earth.

EXAMPLE 3

Phosphosulfurized 1,2-Dodecanediol

Commercially obtained 1,2-dodecanediol and phosphorus pentasulfide were reacted as generally described in Example 1. Approximately 808 g of 1,2-dodecanediol (obtained commercially from Viking Chemical Co. as Vikol 12, which contains 12.9% vicinal glycol and about 0.3% oxirane oxygen) and 808 g of toluene were added to a 3 liter reactor fitted as in Example 1. The mixture was warmed to 65° C. with agitation and 222 g of phosphorus pentasulfide was added over 1 hour. The reaction temperature was raised to 85° C. and held for five additional hours with agitation and a nitrogen purge of the vapor space. The mixtures was filtered to remove any unreacted phosphorus pentasulfide.

EXAMPLE 4

Zinc Salt of Phosphosulfurized 1,2-Dodecanediol

Approximately 500 g of the solvent-diluted phosphosulfurized 1,2-dodecanediol described in Example 3 was charged to a 1 liter stirred glass reactor and warmed to about 65° C. Approximately 24 g of zinc oxide was added and the reaction mixture was held at 90° C. with agitation for 5 hours. The solvents were removed by vacuum distillation at 90° C. and the zinc salt was filtered through diatomaceous earth.

EXAMPLE 5

Phosphosulfurized 1,2-Mixed $C_{15}$–$C_{18}$ Alkanediols

Approximately 1060 g of 1,2-mixed $C_{15}$–$C_{18}$ alkanediols (obtained commercially as Vikol 15-18 from Viking Chemical Co., which contains approximately 28%, 1,2-pentadecanediol, 28% 1,2-hexadecanediol, 28% 1,2-heptadecanediol and 16% 1,2-octadecanediol and more than 10% vicinal hydroxyl) was charged to a 5 liter flask equipped as described in Example 1. Approximately 530 g of toluene was added and the reactant was warmed to 70° C. Over a period of one hour, 333 g of phosphorus pentasulfide was added with agitation. The reactants were warmed to 90° C. and held for an additional 5 hours until $H_2S$ evolution slowed. The mixture was filtered to remove any unreacted phosphorus pentasulfide.

EXAMPLE 6

Zinc Salt of Phosphosulfurized 1,2-Mixed $C_{15}$–$C_{18}$ Alkanediols

Approximately 920 g of solvent-diluted phosphosulfurized 1,2-mixed $C_{15}$–$C_{18}$ alkanediols described in Example 5 was charged to a 3 liter reactor and warmed to about 50° C. Approximately 200 g of 2-propanol, 2 g of water, and 70 g of zinc oxide were added. The reaction mixture was heated to 90° C. and held at that temperature for 5 hours with agitation. The zinc salt was filtered through diatomaceous earth and the solvents were removed with vacuum distillation.

EVALUATION OF PRODUCTS

The compounds were evaluated as friction modifiers in accordance with the following test.

LOW VELOCITY FRICTION APPARATUS

Description

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12–13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of $U_k$ vs. speed are taken at 240, 300, 400, and 500 psi. Freshly polished steel specimens are used for each run. The surface of the steel is parallel ground to 4–8 microinches.

The data obtained are shown in Table 1. The data in Table 1 are reported as percent reduction in coefficient of friction at two speeds. The friction-reducing ester additives were evaluated in a fully formulated 5W-20 synthetic lubricating oil comprising an additive package including anti-oxidant, detergent, dispersant and inhibitors. The oil had the following general characteristics:

| | |
|---|---|
| Viscosity 100° C. | 6.8 cs |
| Viscosity 40° C. | 36.9 cs |
| Viscosity Index | 143 |

TABLE 1

| | Additive Conc. Wt. % | % Change in Coefficient of Friction @ | |
|---|---|---|---|
| | | 5 Ft./Min. | 30 Ft./Min. |
| Base Fluid | — | 0 | 0 |
| Example 2 | 2 | 36 | 29 |
| | 1 | 29 | 27 |
| Example 4 | 2 | 17 | 13 |
| Example 6 | 4 | 24 | 21 |

These salts were relatively non-corrosive to copper as measured in 200″ solvent paraffinic neutral lubricating oil using the ASTM D130-80 Copper Strip Corrosion Test.

TABLE 2

| | Copper Strip Corrosivity | | |
|---|---|---|---|
| | Additive Conc. Wt. % | Test Rating | |
| | | ASTM D130-80 3 Hrs. @ 250° F. | ASTM D130-80 6 Hrs. @ 210° F. |
| Example 2 | ½ | — | 2C |
| | 1 | 2C | 1B |
| Example 4 | ½ | — | 2C |
| Example 6 | ½ | — | 2D |
| | 1 | — | 2D |
| | 3 | — | 2A |

Representative samples of the above prepared compositions were also evaluated for antioxidant properties with a catalytic oxidation test. Samples of 200″ solvent paraffinic neutral mineral lubricating oil were placed in an oven at 325° F. Present in the samples were the following metals, either known to catalyze organic oxidation or commonly used materials of construction:

a. 15.6 sq. in. of sand-blasted iron wire
b. 0.78 sq. in. of polished copper wire
c. 0.87 sq. in. of polished aluminum wire
d. 0.167 sq. in. of polished lead surface Dry air was passed through the sample at a rate of about 5 liters per hour for 40 hours. Table 3 shows the data.

TABLE 3

| | Catalytic Oxidation Test 40 Hours @ 325° F. | | |
|---|---|---|---|
| | Additive Conc Wt. % | Lead Loss, mg | % Increase in Viscosity of Oxidized Oil Using KV @ 210° F. | Neut No., NN |
| Base Oil | — | −1.2 | 67 | 3.62 |
| Example 2 | ½ | 0.4 | — | 1.24 |
| Example 4 | 1 | 0.1 | 6 | 1.47 |
| | 3 | 0.2 | 8 | 2.38 |
| Example 6 | ½ | 0.2 | 50 | 2.67 |
| | 1 | 0.2 | 29 | 2.68 |
| | 3 | 0.2 | 15 | 2.08 |

I claim:

1. A reaction product formed by reacting a 1,2-$C_{15}$ through $C_{18}$ alkane vicinal diol mixture with a phosphorus polysulfide, followed by reacting the product thus obtained with a metal containing compound.

2. The product of claim 1 in which the phosphorus polysulfide is phosphorus pentasulfide.

3. The product of claim 1 in which the metal is from Groups IB, IIB, VIA and VIII of the Periodic Table.

4. The product of claim 3 in which the metal is derived from salts, oxides, hydroxides, carbonates, chlorides or mixtures thereof.

5. The product of claim 3 in which the metal is silver, cadmium, zinc, molybdenum, nickel or mixtures thereof.

6. The product of claim 1 in which the hydrocarbyl vicinal diol is mixed $C_{15}$-$C_{18}$ alkanediols, the phosphorus polysulfide is phosphorus pentasulfide and the metal-containing compound is zinc oxide.

7. A lubricant composition comprising a major proportion of a lubricant and a friction reducing amount of a reaction product formed by reacting a 1,2-$C_{15}$ through $C_{18}$ alkane vicinal diol mixture with a phosphorus polysulfide, followed by reacting the product thus obtained with a metal-containing compound.

8. The composition of claim 7 in which the phosphorus polysulfide is phosphorus pentasulfide.

9. The composition of claim 7 in which the metal is from Groups IB, IIB, VIA and VIII of the Periodic Table.

10. The composition of claim 9 in which the metal is derived from salts, oxides, hydroxides, carbonates, chlorides or mixtures thereof.

11. The composition of claim 9 in which the metal is silver, cadmium, zinc, molybdenum, nickel or mixtures thereof.

12. The composition of claim 7 in which in said product the hydrocarbyl vicinal diol is mixed $C_{15}$-$C_{18}$ alkanediols, the phosphorus polysulfide is phosphorus pentasulfide and the metal-containing compound is zinc oxide.

13. The composition of claims 7, 8, 9, 10, 11 or 12 in which said lubricant is (1) a lubricating oil, (2) a mixture of lubricating oils, or (3) a grease from (1) or (2).

14. The composition of claim 13 wherein the lubricating oil is a mineral oil.

15. The composition of claim 14 wherein the lubricating oil is a synthetic mineral oil.

16. The composition of claim 7 wherein the lubricant is a mixture of mineral and synthetic lubricating oils.

17. The composition of claim 13 wherein said lubricant is said grease.

* * * * *